United States Patent
Ito et al.

(12)

(10) Patent No.: US 6,562,331 B1
(45) Date of Patent: May 13, 2003

(54) MATING DISRUPTION METHODS FOR THE CONTROL OF INSECT PESTS

(75) Inventors: Tatsuya Ito, Niigata-ken (JP);
Takehiko Fukumoto, Niigata-ken (JP);
Kinya Ogawa, Tokyo (JP); Fumiaki Mochizuki, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/635,905

(22) Filed: Aug. 10, 2000

(30) Foreign Application Priority Data

Aug. 13, 1999  (JP) ............................................. 11-229028
Aug. 13, 1999  (JP) ............................................. 11-229029

(51) Int. Cl.$^7$ ......................... A01N 25/00; A01N 35/00
(52) U.S. Cl. ................... 424/84; 47/1.01 R; 47/1.01 F;
47/9; 47/20.1; 47/32; 47/58.1 R; 47/58.1 SC;
514/693; 514/703; 514/769; 514/772; 514/772.1;
514/772.2; 514/772.3; 514/772.5; 514/772.6
(58) Field of Search ............................ 424/84; 514/693,
514/703, 769, 772, 772.1, 772.2, 772.3,
772.5, 772.6; 47/58.1, 1.5, 5.5, 9, 28.1,
32, 1.01 R, 1.01 F, 20.1, 58.1 R, 58.1 SC

(56) References Cited

U.S. PATENT DOCUMENTS 5,750,129 A    5/1998   Wakarchuk ................. 424/408

FOREIGN PATENT DOCUMENTS

| EP | 0710 440 | * 5/1996 |
|----|----------|----------|
| JP | 6-14824  | 3/1994   |
| JP | 09124408 | 5/1997   |

OTHER PUBLICATIONS

Unger et al., Predicting the effect of moisture on vapor–phase sorption of volatile organic compounds to soils, Environ. Sci. Technol. (1996), vol. 30, pp. 1081–1091.*

STN/CAS online, file CROPU, Acc. No. 1997–87832, JP 09124408 (1997), Abstract.*

STN/CAS online, file JICST–EPlus, Acc. No. 1000102423 (Yamaguchi et al., Kankyo Kogaku Kenkyu Ronbunshu (Proceedings of Environmental Engineering Research), (1999) vol. 36, pp. 477–482)), Abstract.*

Yamaguchi et al. Predictive Model for Adsorption of Volatile Organic Chemicals on Soils *Environmental Engineering Research* 36, 477–482 (1999).

* cited by examiner

Primary Examiner—Jose' G. Dees
Assistant Examiner—Frank Choi
(74) Attorney, Agent, or Firm—Myers Bigel Sibley & Sajovec, PA

(57) ABSTRACT

A mating disruption method for the control of insect pests comprises releasing a sex pheromone in a field wherein an adsorption of the sex pheromone to a soil in the field is decreased.

20 Claims, No Drawings

MATING DISRUPTION METHODS FOR THE CONTROL OF INSECT PESTS

BACKGROUND OF THE INVENTION

1. Field of the Invention

This invention relates to mating disruption methods for the control of insect pests wherein a sex pheromone for an insect pest of interest is allowed to hang in the air, so that the mating behavior of the insect pest is disturbed to control the insect pest by interference with mating.

2. Description of the Related Art

In recent years, sex pheromones used in the mating disruption method for the control of insect pests are attracting attention as nontoxic pesticides. According to this pest control method, a synthetic sex pheromone for an insect pest of interest is allowed to hang in the air at a sufficiently high concentration to make males incapable of recognizing the sex pheromone released by females, so that the mating behavior of males is disturbed to interfere with mating.

The most important factor in this method is the synthetic sex pheromone concentration in the air surrounding a group of plants in which the insect pest exhibits mating behavior, and higher concentrations produce a more powerful pest-controlling effect. Since the breeding period of insect pests is usually long, a synthetic sex pheromone is slowly released into the air, for example, with the aid of dispensers. Although higher rates of release give higher concentrations in the air, unduly high rates of release are uneconomical. Accordingly, it is necessary to maintain the highest possible sex pheromone concentration in the air while controlling the release rate of the sex pheromone from dispensers at an economical level.

However, even if an identical amount of a sex pheromone is released in different fields, the resulting mating-disrupting effect may often vary considerably. The reason for this is that, according to the differences in field conditions and meteorological conditions, the sex pheromone may rapidly diffuse from the field to reduce its concentration to a level insufficient for the purpose of mating disruption. In the case of a substantially level field, this problem can be solved by installing air flow shields having a height of not less than 30 cm above the ground in such a way that they lie in the neighborhood of the ground along the outer periphery of the field and they block at least the spaces between the rows of plants and/or the ridges. Similarly, in the case of an inclined field, this problem can be solved by installing air flow shields having a height of not less than 30 cm above the ground on the lower side of the field in such a way that they lie in the neighborhood of the ground at least along the lower side of the outer periphery of the field and they block at least the spaces between the rows of plants and/or the ridges (Japanese Patent Publication (JP-A) No. 6-14824/"94).

However, even if the above-described method is employed, the sex pheromone may show considerable variation in effectiveness and may fail to produce a satisfactory mating-disrupting effect in some cases. The reason for this is that the sex pheromone released from dispensers becomes adsorbed to the soil of the field and, as a result, its concentration is reduced to a level insufficient for the purpose of mating disruption. In such a case, the pest-controlling effect can be enhanced by increasing the release rate of the sex pheromone and thereby elevating its concentration in the air. However, this will cause a wasteful use of expensive sex pheromones.

The adsorption of sex pheromones to soil can occur without respect to their composition. However, among sex pheromones, the amounts of aldehyde type sex pheromones adsorbed to soil are greater than those of acetate type sex pheromones. Consequently, when a sex pheromone mixture composed of an aldehyde and an acetate is released with the aid of dispensers, the compositional ratio of the aldehyde and the acetate in the air may be different from their compositional ratio in the mixture released.

For example, where two or more sex pheromones are released by females, males cannot recognize them unless the composition of the two or more sex pheromones is within a specific range. Accordingly, in order to disturb the mating behavior of males and thereby interfere with mating, an important factor is that the composition of the sex pheromone in the air is within the appropriate compositional range of the sex pheromones released by females. However, if the composition of the sex pheromones in the air goes beyond the limits recognizable by males as a result of their adsorption to the soil, the mating-disrupting effect of the sex pheromones will be reduced to disadvantage.

SUMMARY OF THE INVENTION

The present invention has been made in view of the above-described circumstances, and an object thereof is to provide a mating disruption method for the control of insect pests by means of a sex pheromone which can maintain the sex pheromone concentration in the air surrounding a group of plants at a high level for a long period of time while controlling the release rate of the sex pheromone from dispensers at an economical level, and can hence produce a more powerful mating-disrupting effect by use of a given amount of the sex pheromone.

The present inventors made intensive investigations with a view to solving the above problem, and have now found that, when a sex pheromone is released in a field sprinkled with water so that the soil has a water content of 20 to 100% during the breeding period of insect pests, the sex pheromone is prevented from being adsorbed to the soil and, as a result, the sex pheromone concentration in the air can be maintained at a high level for a long period of time. The present invention has been completed on the basis of this finding.

Moreover, the present inventors have also found that, when a sex pheromone is released in an open field where the surface of the soil is covered with a covering material that is less apt to adsorb sex pheromones than the surface of the soil, or in a house field where the surface of the soil and all or part of the inner surface of the house are covered with a covering material that is less apt to adsorb sex pheromones than the surface of the soil, the sex pheromone is prevented from being adsorbed to the soil and, as a result, the sex pheromone concentration in the air can be maintained at a high level for a long period of time. The present invention has also been completed on the basis of this finding.

The present invention relates to a mating disruption method for the control of insect pests which comprises releasing a sex pheromone in a field wherein an adsorption of the sex pheromone to a soil in the field is decreased.

The mating disruption methods for the control of insect pests by means of a sex pheromone in accordance with the present invention are highly effective in preventing the sex pheromone from being adsorbed to the soil and, as a result, can maintain the sex pheromone concentration in the air at a high level for a long period of time.

DETAILED DESCRIPTION OF THE PREFERRED EMBODIMENTS

The present invention is more specifically described hereinbelow.

A first aspect of the present invention relates to a mating disruption method for the control of insect pests in a field sprinkled with water so that the soil has a water content of 20 to 100% during the breeding period of insect pests. The term "water content" as used herein is defined as follows: The water content of soil dried by heating at 110° C. until a constant mass is reached is regarded as 0%, and the water content of the soil impregnated with an increasing amount of water until the separation of water occurs is regarded as 100%. The water content of 100% comprehends the case in which the soil is covered with water as in paddy fields.

If the water content of soil is less than 20%, sex pheromones (in particular, aldehyde type sex pheromones) are apt to be adsorbed to the soil, so that the concentration thereof will be insufficient for the purpose of mating disruption. Moreover, where two or more sex pheromones including an aldehyde type sex pheromone are released with the aid of dispensers, an unduly low water content of soil will cause a change in the compositional ratio of sex pheromones released into the air, so that they may fail to disturb the mating behavior of males.

In order to impregnate the soil with water, paddy fields and the like may be filled with water, and other fields may be sprinkled with water by means of a sprinkler truck, sprayer or sprinkler. Thus, this can be easily accomplished without requiring any special material or tool.

The mating disruption method of the present invention may be applied to both substantially level fields and inclined fields.

The mating disruption method of the present invention can produce a more powerful mating-disrupting effect when it is applied to a field in which the soil has a specific surface area of not greater than 100 m$^2$/g, preferably not greater than 50 m$^2$/g, as measured by the BET method. Although the well-known methods for measuring specific surface areas include the gas adsorption method, liquid phase adsorption method, immersion method, permeation method and the like, it is preferable that, in the present invention, measurements be made according to the gas adsorption method and, in particular, the BET method. Examples of soil having a specific surface area of not greater than 100 m$^2$/g include sandy soil and clayey soil having a diameter of not less than 0.0001 mm. If the specific surface area of the soil is greater than 100 $m^2/g$, the amount of sex pheromone adsorbed thereto will be increased, water sprinkling may not be easy because of its excellent water-holding capacity, and this soil may not be suitable for agricultural purposes.

In order to release a sex pheromone in the practice of the present invention, there may be employed any method that permits the sex pheromone to be continuously released into the air. This can be accomplished, for example, by using dispensers, polymeric articles impregnated with a sex pheromone, a sprayer, or a partly open vessel. By way of example, the dispensers may comprise polymeric containers formed from a polyolefin (e.g., polyethylene or polypropylene) or a copolymer containing 90% by weight or more of polyethylene (e.g., ethylene-vinyl acetate copolymer), assuming the shape of tubes, capsules, ampules or bags, and having a wall thickness of 0.2 to 1.0 mm.

According to a second aspect of the present invention, there is provided a mating disruption method for the control of insect pests by means of a sex pheromone which comprises releasing a sex pheromone in an open field where the surface of the soil is covered with a covering material that is less apt to adsorb sex pheromones than the surface of the soil, or in a house field where the surface of the soil and all or part of the inner surface of the house are covered with a covering material that is less apt to adsorb sex pheromones than the surface of the soil.

The covering material used in the present invention is a material which can cover the soil or the inner surfaces of the house in order to prevent the sex pheromone from being adsorbed to the surface of the soil and the like. From the viewpoint of ease of application and the like, it is preferable to use a polymeric material designed for agricultural purposes. No particular limitation is placed on the type of the covering material used in the present invention, provided that it is less apt to adsorb sex pheromones than the surface of the soil. However, it is preferable to use a covering material comprising a polymeric material characterized in that the degree of adsorption of the aforesaid sex pheromone at 25° C. is not greater than 5.0%.

The term "degree of adsorption" means the degree of adsorption of a sex pheromone as measured with a circular film specimen formed from a polymeric material and having a film thickness of 0.4 mm and a diameter of 2 cm. This degree of adsorption can be determined according to the following equation.

$$\text{Degree of adsorption}(\%)=\{(\text{Weight of sex pheromone adsorbed to polymeric film})/(\text{Weight of polymeric film})\}\times 100$$

In the measurement of the degree of adsorption, the aforesaid film specimen is soaked in a sex pheromone fluid, and the increment in the weight of the film specimen is regarded as the weight of sex pheromone adsorbed to the polymeric film.

The polymeric material used as the covering material should be characterized in that the degree of adsorption of the sex pheromone at 25° C. is not greater than 5.0% and preferably not greater than 2.0%. If the degree of adsorption of the sex pheromone is greater than 5.0%, sex pheromones (in particular, aldehyde type sex pheromones) are apt to be adsorbed to the polymeric material, so that the concentration thereof may be insufficient for the purpose of mating disruption. Moreover, where two or more sex pheromones including an aldehyde type sex pheromone are released, for example, with the aid of dispensers, an unduly high degree of adsorption of the sex pheromones by the polymeric material may cause a change in the compositional ratio of sex pheromones released into the air, so that they may fail to disturb the mating behavior of males.

The polymeric material used in the present invention, which is less apt to adsorb sex pheromones, may have any of various forms such as film and sheet, provided that it meets the above-described requirements. The degree of adsorption of a sex pheromone is a value peculiar to the polymeric material. Accordingly, if the form of the covering material is changed from a film to a sheet, only the weight of the polymeric material is increase and the amount of sex pheromone adsorbed thereto is increased correspondingly. Thus, the degree of adsorption had an identical value regardless of the fact that the covering material is in the form of a film or sheet.

The polymeric materials which are less apt to adsorb sex pheromones and can be used in the present invention include, for example, polyesters, nylons, polyvinyl alcohol, a saponification product of polyvinyl acetate, polyvinylidene chloride (PVDC), ethylene-vinyl alcohol copolymer, a saponification product of ethylene-vinyl acetate copolymer, polyvinylidene chloride-coated (PVDC-coated) films or sheets, aluminum-laminated films or sheets, and aluminized films or sheets. These materials are used, for example, in the form of films or sheets, and the polymeric sheets may have the shape of a plate. These polymeric films or sheets may be used after they have been subjected to various forming operations such as stretching, foaming, multilayer lamination, lining and surface treatment.

Where the surface of the soil is covered with a polymeric film or sheet, it is sufficient to spread the polymeric film or sheet over the ground and fasten it in place so that it may not be blown away by the wind or the like. In a house field, the adsorption of the sex pheromone can be prevented simply by affixing a polymeric film or sheet to the inner surfaces of the house.

Where the inner surfaces of the house are covered with a polymeric film or sheet which are less apt to adsorb sex pheromones, the adsorption of the sex pheromone can be prevented simply by covering the inner surfaces of the house to a height almost equal to the height of the plants. However, the adsorption of the sex pheromone can be more effectively prevented by covering all of the inner surfaces of the house.

The sex pheromone substance used in the present invention including the first and second aspects may be any compound capable of releasing a sex pheromone with the aid of dispensers or the like. Examples thereof include aliphatic acetate compounds of 10 to 18 carbon atoms, alcohol compounds of 10 to 18 carbon atoms, aldehyde compounds of 10 to 18 carbon atoms, ketone compounds of 10 to 18 carbon atoms, and hydrocarbon compounds of 10 to 18 carbon atoms.

More specifically, the aliphatic acetate compounds of 10 to 18 carbon atoms include aliphatic acetates having a straight-chain, branched or cyclic alkyl or alkylene group of 10 to 18 carbon atoms, the alcohol compounds of 10 to 18 carbon atoms include aliphatic alcohols having a straight-chain, branched or cyclic alkyl or alkylene group of 10 to 18 carbon atoms, the ketone compounds of 10 to 18 carbon atoms include aliphatic ketones having a straight-chain, branched or cyclic alkyl or alkylene group of 10 to 18 carbon atoms, and the hydrocarbon compounds of 10 to 18 carbon atoms include hydrocarbon compounds having a straight-chain, branched or cyclic alkyl or alkylene group of 10 to 18 carbon atoms.

All of these sex pheromone compounds exhibit adsorption to the soil. Among others, the aldehyde compounds are very likely to be adsorbed to the soil and the like. Accordingly, the present invention can prevent adsorption of these sex pheromones and thereby produce a marked effect thereon.

The aldehyde type sex pheromones to which the present invention can be applied are aldehyde compounds of 10 to 18 carbon atoms. Specific examples thereof include Z5-decenal, n-dodecanol, Z5-dodecenal, Z7-dodecenal, Z9-dodecenal, E5Z7-dodecadienal, Z5E7-dodecadienal, Z5Z7-dodecadienal, E7Z9-dodecadienal, E8E10-dodecadienal, E8E10-dodecadienal, E8Z10-dodecadienal, E9,11-dodecadienal, Z9,11-dodecadienal, n-tetradecanal, Z5-tetradecenal, Z7-tetradecenal, Z9-tetradecenal, E11-tetradecenal, Z11-tetradecenal, E8E10-tetradecadienal, Z9E11-tetradecadienal, Z9Z11-tetradecadienal, Z9E12-tetradecadienal, E11,13-tetradecadienal, Z11,13-tetradecadienal, Z9E11,13-tetradecatrienal, Z10-pentadecenal, E9Z11-pentadecadienal, n-hexadecanal, Z7-hexadecenal, Z9-hexadecenal, E10-hexadecenal, Z10-hexadecenal, E11-hexadecenal, Z11-hexadecenal, E6Z11-hexadecadienal, Z7E11-hexadecadienal, Z7Z11-hexadecadienal, E9Z11-hexadecadienal, Z9E11-hexadecadienal, Z9E12-hexadecadienal, E10E12-hexadecadienal, E10Z12-hexadecadienal, Z10E12-hexadecadienal, E11E13-hexadecadienal, E11Z13-hexadecadienal, Z11E13-hexadecadienal, Z11Z13-hexadecadienal, E4E6Z11-hexadecatrienal, E10E12E14-hexadecatrienal, E10E12Z14-hexadecatrienal, n-octadecanal, E2-octadecenal, E9-octadecenal, E11-octadecenal, Z11-octadecenal, E13-octadecenal, Z13-octadecenal, E14-octadecenal, E2Z13-octadecadienal, Z3Z13-octadecadienal, Z9Z12-octadecadienal, E11E14-octadecadienal, Z13Z15-octadecadienal and Z9Z12Z15-octadecatrienal.

The mating disruption method for the control of insect pests in accordance with the present invention can produce a marked effect not only when any of the above-described aldehyde compounds is used alone, but also when a plurality of compounds (e.g., an aldehyde compound and an acetate compound, or an aldehyde compound and an alcohol compound) are used as sex pheromones for insect pests. In the first aspect of the present invention, the reason therefor is that, since soil having a specific water content is highly effective in preventing sex pheromones (in particular, aldehyde compounds) from being adsorbed to the soil, the compositional ratio of sex pheromones released in the field can be maintained at a predetermined value. In the second aspect of the present invention, the reason therefor is that, since covering with a polymeric film or sheet is highly effective in preventing sex pheromones (in particular, aldehyde compounds) from being adsorbed to the soil, and since sex pheromones (in particular, aldehyde compounds) are scarcely adsorbed to the polymeric film or sheet, the compositional ratio of sex pheromones released in the field can be maintained at a predetermined value.

In order to release a sex pheromone in the practice of the present invention including the first and second aspects, there may be employed any method that permits the sex pheromone to be continuously released into the air. This can be accomplished, for example, by using dispensers, polymeric articles impregnated with a sex pheromone, a sprayer, or a partly open vessel.

By way of example, the dispensers may comprise polymeric containers formed from a polyolefin (e.g., polyethylene or polypropylene) or a copolymer containing 90% by weight or more of polyethylene (e.g., ethylene-vinyl acetate copolymer), assuming the shape of tubes, capsules, ampules or bags, and having a wall thickness of 0.2 to 1.0 mm.

The present invention is further illustrated by the following examples and comparative examples. However, these examples are not to be construed to limit the scope of the invention.

EXAMPLE 1

Using a desiccator having a diameter of 22 cm and a height of 20 cm and provided with two threaded openings at the top and in the sidewall, soil which had been dried by heating at 110° C. for 2 hours and then impregnated with water until the separation of water occurred (to a water content of 100%) was charged thereinto to a depth of 7 cm as measured from the bottom of the desiccator. In this desiccator, a sustained release sex pheromone preparation comprising a plastic container (polyethylene tube) measuring 1.07 mm in inner diameter, 1.73 mm in outer diameter, and 200 mm in length, and having sealed therein a sex pheromone mixture (120 g) composed of 5 parts by weight of Z11-tetradecenal (Z11-16:Ald) and 5 parts by weight of Z11-tetradecenyl acetate (Z11-16:Ac) was broken in two and placed on the soil with the aid of a support. Then, a 250 ml collection bottle containing 200 ml of hexane was connected to the upper opening of the desiccator by means of a teflon tube, and a suction pump was further connected to the collection bottle. Thus, Z11-tetradecenal and Z11-tetradecenyl acetate released in the desiccator were collected for about 4 hours, and the amounts thereof were analyzed.

Analysis was made by subjecting the collecting hexane solution to gas chromatography and determining the pheromones according to the internal standard method. The results thus obtained are shown in Table 1.

Comparative Example 1

According to the same procedure as described in Example 1, soil which had been dried by heating at 110° C. for 2 hours was charged into a desiccator, and a sustained release sex pheromone preparation comprising a plastic container having 5 parts by weight of Z11-tetradecenal and 5 parts by weight of Z11-tetradecenyl acetate sealed therein was placed thereon with the aid of a support. Using the same solvent as used in Example 1, Z11-tetradecenal and Z11-tetradecenyl acetate released in the desiccator were collected for the same time and determined. The results thus obtained are shown in Table 1.

EXAMPLE 2

According to the same procedure as described in Example 1, soil which had been dried by heating at 110° C. for 2 hours and then impregnated with 20% of water was charged into a desiccator, and a sustained release sex pheromone preparation comprising a plastic container having 5 parts by weight of Z11-tetradecenal and 5 parts by weight of Z11-tetradecenyl acetate sealed therein was placed thereon with the aid of a support. Using the same solvent as used in Example 1, Z11-tetradecenal and Z11-tetradecenyl acetate released in the desiccator were collected for the same time and determined. The results thus obtained are shown in Table 1.

TABLE 1

| | Analytical values ($\mu$g) | | Weight ratio |
| --- | --- | --- | --- |
| | Z11-tetradecenal | Z11-tetradecenyl acetate | Aldehyde/ acetate |
| Example 1 | 23 | 8 | 3.0 |
| Example 2 | 15 | 8 | 1.9 |
| Comparative Example 1 | 10 | 9 | 1.1 |

EXAMPLE 3

Sustained release sex pheromone preparations were made by mixing 7 parts by weight of a rice stem borer (*Chilo Suppressalis*) sex pheromone fluid (composed of 77 parts by weight of Z11-hexadecenal (Z11-16:Ald), 8 parts by weight of Z9-hexadecenal (Z9-16:Ald), and 15 parts by weight of Z13-octadecenal (Z13-18:Ald)) with 3 parts by weight of n-tetradecenyl acetate (n-14:Ac) to form a sex pheromone-containing mixture, and sealing this mixture in plastic containers (polyethylene tubes) measuring 1.40 mm in inner diameter, 2.60 mm in outer diameter, and 200 mm in length.

In a 10 hectare paddy field (in Tatebayashi City, Gunma Prefecture, Japan) filled with water, sticks having the aforesaid sex pheromone preparations attached thereto were uniformly installed at a density of 250 sticks per 10 ares. Using this sex pheromone-treated field, the concentrations of Z11-hexadecenal and n-tetradecenyl acetate in the air were determined.

Specifically, a pole was set up at the center of this sex pheromone-treated field, and an absorption tube packed with 100 g of fibrous activated carbon was attached thereto at a height of 50 cm above the ground. Moreover, a suction pump was connected to the absorption tube, and suction was carried out for a period of 8 hours extending from 8 o'clock in the evening to 4 o'clock in the next morning to collect the sex pheromones present in the air. After collection, the activated carbon was extracted with n-hexane, and the extract was analyzed by gas chromatography. Thus, the concentrations of Z11-hexadecenal and n-tetradecenyl acetate in the air were determined. The results thus obtained are shown in Table 2.

Comparative Example 2

Similarly to Example 3, sustained release sex pheromone preparations were made by mixing 7 parts by weight of a rice stem borer sex pheromone fluid [composed of 77 parts by weight of Z11-hexadecenal, 8 parts by weight of Z9-hexadecenal, and 15 parts by weight of Z13-octadecenal] with 3 parts by weight of n-tetradecenyl acetate (n-14:Ac) to form a sex pheromone-containing mixture, and sealing this mixture in plastic containers.

Thereafter, the same procedure as described in Example 3 was repeated, except that a 10 hectare paddy field (in Tatebayashi City, Gunma Prefecture, Japan) which had been completely drained off was used for the sex pheromone-treated field. Using this sex pheromone-treated field, the concentrations of Z11-hexadecenal and n-tetradecenyl acetate in the air were determined. The results thus obtained are shown in Table 2.

TABLE 2

| | Analytical values (ng/m$^3$) | | Weight ratio |
| --- | --- | --- | --- |
| | Z11-hexadecenal | n-tetradecenyl acetate | Aldehyde/ acetate |
| Example 3 | 36 | 5 | 7.2 |
| Comparative Example 2 | 15 | 4 | 3.8 |

EXAMPLE 4

Using a desiccator having a diameter of 22 cm and a height of 20 cm and provided with two threaded openings at the top and in the sidewall, soil which had been dried by heating at 110° C. for 2 hours was charged thereinto to a depth of 7 cm as measured from the bottom of the desiccator. The surface of the soil and the inner surfaces surrounding the upper space of the desiccator were covered with a film of a saponification product of ethylene-vinyl acetate copolymer (trade name: Vinylon np, manufactured by Aicello Chemical Co., Ltd.). In this desiccator, a sustained release sex pheromone preparation comprising a plastic container (polyethylene tube) measuring 1.07 mm in inner diameter, 1.73 mm in outer diameter, and 200 mm in length, and having sealed therein a sex pheromone mixture (120 g) composed of 5 parts by weight of Z11-tetradecenal (Z11-16:Ald) and 5 parts by weight of Z11-tetradecenyl acetate (Z11-16:Ac) was broken in two and placed on the soil with the aid of a support. Then, a 250 ml collection bottle containing 200 ml of hexane was connected to the upper opening of the desiccator by means of a teflon tube, and a suction pump was further connected to the collection bottle. Thus, Z11-tetradecenal and Z11-tetradecenyl acetate released in the desiccator were collected for about 4 hours, and the amounts thereof were measured.

The measurement was made by subjecting the collecting hexane solution to gas chromatography and determining the pheromones according to the internal standard method. The results thus obtained are shown in Table 3.

Comparative Example 3

According to the same procedure as described in Example 4, soil which had been dried by heating at 110° C. for 2 hours was charged into a desiccator, and a sustained release sex pheromone preparation comprising a plastic container having 5 parts by weight of Z11-tetradecenal and 5 parts by weight of Z11-tetradecenyl acetate sealed therein was placed thereon with the aid of a support. Using the same solvent as used in Example 4, Z11-tetradecenal and Z11-tetradecenyl acetate released in the desiccator were collected for the same time and determined. The results thus obtained are shown in Table 3.

TABLE 3

| | Analytical values (μg) | | Weight ratio |
|---|---|---|---|
| | Z11-tetradecenal | Z11-tetradecenyl acetate | Aldehyde/ acetate |
| Example 4 | 26 | 8 | 3.3 |
| Comparative Example 3 | 10 | 9 | 1.1 |

What is claimed is:

1. A mating disruption method for the control of insect pests comprising:
   decreasing the ability of a soil in a field to adsorb a sex pheromone;
   by sprinkling the field with water so that the soil has a water content of 20 to 100% during the breeding period of insect pests; and
   releasing the sex pheromone in the field.

2. The mating disruption method for the control of insect pests according to claim 1 wherein the soil of said field has a specific surface area of not greater than 100 m²/g as measured by the BET method.

3. The mating disruption method for the control of insect pests according to claim 2 wherein said sex pheromone contains at least one component selected from among aldehydes of 10 to 18 carbon atoms.

4. The mating disruption method for the control of insect pests according to claim 1 wherein said sex pheromone contains at least one component selected from among aldehydes of 10 to 18 carbon atoms.

5. A mating disruption method for the control of insect pests comprising:
   decreasing the ability of a soil in a field to adsorb a sex pheromone; and
   releasing the sex pheromone in an open field where the surface of the soil is covered with a covering material that is less apt to adsorb sex pheromones than the surface of the soil.

6. The mating disruption method for the control of insect pests according to claim 5 wherein said covering material comprises a polymeric material having 5.0% or less in the degree of adsorption of said sex pheromone at 25° C.

7. The mating disruption method for the control of insect pests according to claim 6 wherein said covering material is selected from among polyesters, nylons, polyvinyl alcohol, a saponification product of polyvinyl acetate, polyvinylidene chloride, ethylene-vinyl alcohol copolymer, a saponification product of ethylene-vinyl acetate copolymer, polyvinylidene chloride-coated films or sheets, aluminum-laminated films or sheets, and aluminized films or sheets.

8. The mating disruption method for the control of insect pests according to claim 7 wherein said sex pheromone contains at least one component selected from among aldehydes of 10 to 18 carbon atoms.

9. The mating disruption method for the control of insect pests according to claim 6 wherein said sex pheromone contains at least one component selected from among aldehydes of 10 to 18 carbon atoms.

10. The mating disruption method for the control of insect pests according to claim 5 wherein said covering material is selected from among polyesters, nylons, polyvinyl alcohol, a saponification product of polyvinyl acetate, polyvinylidene chloride, ethylene-vinyl alcohol copolymer, a saponification product of ethylene-vinyl acetate copolymer, polyvinylidene chloride-coated films or sheets, aluminum-laminated films or sheets, and aluminized films or sheets.

11. The mating disruption method for the control of insect pests according to claim 10 wherein said sex pheromone contains at least one component selected from among aldehydes of 10 to 18 carbon atoms.

12. The mating disruption method for the control of insect pests according to claim 5 wherein said sex pheromone contains at least one component selected from among aldehydes of 10 to 18 carbon atoms.

13. A mating disruption method for the control of insect pests comprising:
   decreasing the ability of a soil in a field to adsorb a sex pheromone; and
   releasing the sex pheromone in a green house field where the surface of the soil and all or part of the inner surface of the house are covered with a covering material that is less apt to adsorb sex pheromones than the surface of the soil.

14. The mating disruption method for the control of insect pests according to claim 13 wherein said covering material comprises a polymeric material having 5.0% or less in the degree of adsorption of said sex pheromone at 25° C.

15. The mating disruption method for the control of insect pests according to claim 14 wherein said covering material is selected from among polyesters, nylons, polyvinyl alcohol, a saponification product of polyvinyl acetate, polyvinylidene chloride, ethylene-vinyl alcohol copolymer, a saponification product of ethylene-vinyl acetate copolymer, polyvinylidene chloride-coated films or sheets, aluminum-laminated films or sheets, and aluminized films or sheets.

16. The mating disruption method for the control of insect pests according to claim 15 wherein said sex pheromone contains at least one component selected from among aldehydes of 10 to 18 carbon atoms.

17. The mating disruption method for the control of insect pests according to claim 14 wherein said sex pheromone contains at least one component selected from among aldehydes of 10 to 18 carbon atoms.

18. The mating disruption method for the control of insect pests according to claim 13 wherein said covering material is selected from among polyesters, nylons, polyvinyl alcohol, a saponification product of polyvinyl acetate, polyvinylidene chloride, ethylene-vinyl alcohol copolymer, a saponification product of ethylene-vinyl acetate copolymer, polyvinylidene chloride-coated films or sheets, aluminum-laminated films or sheets, and aluminized films or sheets.

19. The mating disruption method for the control of insect pests according to claim 18 wherein said sex pheromone contains at least one component selected from among aldehydes of 10 to 18 carbon atoms.

20. The mating disruption method for the control of insect pests according to claim 13 wherein said sex pheromone contains at least one component selected from among aldehydes of 10 to 18 carbon atoms.

* * * * *